US008387266B2

(12) United States Patent
Eddy

(10) Patent No.: US 8,387,266 B2
(45) Date of Patent: Mar. 5, 2013

(54) DEVICE FOR MEASURING A BODY PART OF A LIVING BEING

(75) Inventor: Patrick E. Eddy, Allendale, MI (US)

(73) Assignee: Medical Minds LLC, Allendale, MI (US)

( * ) Notice: Subject to any disclaimer, the term of this patent is extended or adjusted under 35 U.S.C. 154(b) by 0 days.

(21) Appl. No.: 13/132,405

(22) PCT Filed: Dec. 2, 2009

(86) PCT No.: PCT/US2009/066342
§ 371 (c)(1),
(2), (4) Date: Jun. 2, 2011

(87) PCT Pub. No.: WO2010/065590
PCT Pub. Date: Jun. 10, 2010

(65) Prior Publication Data
US 2011/0242549 A1    Oct. 6, 2011

Related U.S. Application Data

(60) Provisional application No. 61/119,235, filed on Dec. 2, 2008, provisional application No. 61/221,650, filed on Jun. 30, 2009.

(51) Int. Cl.
*A61B 5/103* (2006.01)
(52) U.S. Cl. .................. 33/512; 33/706; 33/DIG. 21
(58) Field of Classification Search .................. 33/512, 33/706, 707, 708, DIG. 21
See application file for complete search history.

(56) References Cited

U.S. PATENT DOCUMENTS

| 4,406,544 | A | | 9/1983 | Takada et al. | |
|---|---|---|---|---|---|
| 4,691,565 | A | * | 9/1987 | Theurer | 73/146 |
| 5,038,491 | A | * | 8/1991 | Tsukiji et al. | 33/702 |
| 5,793,201 | A | * | 8/1998 | Nelle et al. | 33/706 |
| 6,658,754 | B2 | * | 12/2003 | Omi | 33/706 |
| 7,571,552 | B2 | * | 8/2009 | McAdam | 33/706 |
| 2002/0029488 | A1 | * | 3/2002 | Nishi | 33/706 |
| 2008/0282566 | A1 | * | 11/2008 | Holzapfel | 33/707 |
| 2009/0021349 | A1 | * | 1/2009 | Errico et al. | 340/5.82 |
| 2009/0119940 | A1 | * | 5/2009 | Meichle et al. | 33/708 |
| 2009/0271998 | A1 | * | 11/2009 | Carlen et al. | 33/706 |

OTHER PUBLICATIONS

United States Patent Publication No. 2008-0021349A1, Jan. 24, 2008, Sakai et al.
United States Patent Publication No. 2005-0222516A1, Oct. 6, 2005, Kasahara et al.
United States Patent Publication No. 2007-0253004A1, Nov. 1, 2007, Noam et al.

* cited by examiner

*Primary Examiner* — G. Bradley Bennett
(74) *Attorney, Agent, or Firm* — Price Heneveld LLP

(57) ABSTRACT

A body limb measurement device (10) comprising a track (12), a cart (14), and a laser source (16) fixedly attached to the cart. The cart is capable of linearly moving along the track. The device can further include a vertical support (18) having a pivot (20), and the track can comprise a pivot receiver (22), wherein the pivot receiver (22) is rotatably attached to the pivot (20). The track (12) can include units of length measurement (24) embedded therein. The cart (14) can include a reference point (26) to correspond to the units of length measurement, to track the cart's position on the track (12). A method of measuring a body part (28) comprising the steps of moving the cart (14) along the track (12) to measure the distance between a first edge (32) and a second edge (34) of the body part (28).

10 Claims, 5 Drawing Sheets

DEVICE FOR MEASURING A BODY PART OF A LIVING BEING

CROSS-REFERENCE TO RELATED APPLICATIONS

This application claims the benefit of U.S. Provisional Application No. 61/221,650, filed Jun. 30, 2009, and U.S. Provisional Application No. 61/119,235, filed Dec. 2, 2008. Both said provisional applications are incorporated herein in their entireties.

BACKGROUND

The present invention generally relates to a device and method for measuring a body part of a being, such as a limb (including a leg), and especially a body party receiving treatment for various circulatory disorders. More specifically the present invention relates to a device and method for measuring a body part using laser beams and without physically touching the body part to be measured.

The inventive device and method may be used to measure the thickness of a body part suffering from any or all of the following circulatory disorders: deep vein thrombosis (DVT), lymphedema, chronic venous insufficiency (CVI), varicose veins, and peripheral arterial disease (PAD). The circulatory disorders often make a body part thicker than normal. The inventive device may also be used to measure the extent of swelling in body parts resulting from any cause.

Deep Vein Thrombosis is a blood clot that can form in a person's legs and sometimes move to his or her lungs, where it could potentially be fatal. DVT is usually caused by immobility. DVT is commonly treated with compression devises.

DVT kills 200,000 Americans each year, more than AIDS and breast cancer combined. 74% of Americans do not know of the condition or symptoms. This little known condition hospitalizes 600,000 people each year. About 2 million people in the United States have a pulmonary embolism each year and more than 10% die from it. Nine out of ten cases of pulmonary embolism are caused by blood clots that form in the legs and then travel to the lungs. Most who die from DVT do so within 30-60 minutes after symptoms start. Pulmonary embolisms occur equally in men and women. The risk of having a pulmonary embolism doubles for every 10 years after the age of 60.

Lymphedema is an abnormal build up of lymph fluid which occurs when a lymph system becomes blocked or impaired. Usually, the affected area involves an extremity. Lymphedema causes the extremity to swell and become heavy and limited in mobility and function. Lymphedema is commonly treated with compression devices. Primary lymphedema is present at birth and effects 2,000,000 people worldwide, effects 10 women to every 1 man, and effects 10 legs to every 1 arm.

Secondary lymphedema is caused by scarring, injury to, or removal of lymph nodes. Secondary lymphedema effects 25,000,000 people worldwide and 2.5 million in the United States.

Chronic venous insufficiency (CVI) is a condition where blood pools in the veins of the lower legs. The veins return blood to the heart from all the body's organs. To do this the calf muscles and the muscles in the feet need to contract with each step to squeeze the veins and push the blood upward. To keep the blood flowing up, and not back down, the veins contain one-way valves. Chronic venous insufficiency occurs when these valves become damaged, allowing the blood to leak backward and pool. Massage techniques are currently used for treatment, along with pressure stockings and compression. Sometimes bypass surgery or valve repair is required.

CVI is a significant public health problem in the United States. About 2-5% of all Americans have change associated with CVI. Approximately 24 million Americans have varicose veins and approximately 6 million Americans have skin changes associated with CVI. Venous stasis ulcers affect approximately 500,000 people. The mean incidence for hospital admission for CVI is 92 per 100,000 admissions. CVI can lead to leg ulcers which can be severe and are responsible for 100,000 cases of disability in the United States alone. Incidences of CVI typically occur in women aged 40-49 and men aged 70-79.

Varicose veins are swollen veins that you can see through the skin. They often look blue, bulging, and twisted. Left untreated, varicose veins may worsen over time. Large varicose veins can cause aching and feelings of fatigue as well as skin changes like rashes, redness, and sores. There are three kinds of veins in a person's legs: the superficial veins, which lie closest to the skin, the deep veins, which lie in groups of muscles, and perforating veins, which connect the superficial veins to the deep veins. The deep veins lead to the vena cava, the body's largest vein, which runs directly to the heart. Varicose veins occur in the superficial veins in your legs.

When a person is in the upright position, the blood in his or her leg veins must work against gravity to return to the heart. To accomplish this, the leg muscles squeeze the deep veins of the legs and feet. One-way flaps, called valves, in the veins keep blood flowing in the right direction. When the leg muscles contract, the valves inside the veins open. When the legs relax, the valves close. This prevents blood from flowing in reverse, back down the legs. The entire process of sending blood back to the heart is called the venous pump. Varicose veins are commonly treated with compression devices, sclerotherapy, ablation, laser treatment, or vein stripping.

As many as 40 million Americans, most of them women, have varicose veins. Fifty percent of all women will suffer from varicose veins by their mid-50s.

When the arteries in the legs become blocked, the legs do not receive enough blood or oxygen. This may be due to a condition called peripheral artery disease (PAD), sometimes called leg artery disease. PAD is commonly treated by lifestyle changes, compression devices, medication, exercise, angioplasty/stenting, bypass surgery, endarterectomy, or amputation. One in three people age 70 or older has PAD. PAD affects about 8 million Americans. Persons with PAD also have four to five times higher risk of a heart attack or stroke.

The above conditions affect tens of millions of people. One common treatment opportunity is using compression devices.

In treatment of the aforementioned circulatory disorders, and especially lymphedema, it becomes necessary to measure the thickness of the affected limb or other body part, to determine whether a particular mode of treatment (especially compression therapy) is working. Some lymphedema (like genital lymphedema) is difficult to measure with antiquated devices such as a tape measure. The present invention measures swelling or thickness without physical contact and can measure lymphedema in any body area.

SUMMARY OF THE INVENTION

Described herein is an apparatus to measure the thickness of a body part, such as a limb. A method of using the apparatus to measure the thickness of the body part is additionally described herein.

More specifically, described herein is a body part measurement device comprising a track, a cart, and a laser source fixedly attached to the cart. The cart is capable of linearly moving along the track. The device can further comprise a vertical support, the vertical support comprising a pivot, the track comprising a pivot receiver, wherein the pivot receiver is rotatably attached to the pivot. The track can comprise units of length measurement, such as a ruler. The cart can include a reference point to correspond to the units of length measurement, such as a pointer located above the units of length measurement. The cart can include an electronic scale (like those found on milling machines or turning centers) that have the ability to zero-out and then measure its own linear travel in small increments (such as increments of 0.0005 inch). In such a case, the cart can have a digital display showing pertinent data (like distance traveled).

In addition, described herein is a method of measuring a body part comprising the steps of: (i) presenting a body part comprising a thickness defined by a first edge and a second edge; (ii) placing the body part between a screen and a body part measurement device comprising: (a) a track; (b) a cart; and (c) a laser source fixedly attached to the cart capable of emitting a laser beam, wherein the cart is capable of linearly moving along the track; (iii) moving the cart along the track until the laser beam emitted from the laser source appears between the first edge and the second edge of the body part; (iv) moving the cart along the track so that the laser beam emitted appears to be moving towards the first edge of the body part until the laser beam emitted from the laser source first appears on the screen; (v) stopping the cart; (vi) accounting for the position of the cart along the track as point X; (vii) moving the cart along the track towards the second edge of a body part until the laser beam emitted from the laser source first appears on the screen; (viii) stopping the cart; (ix) accounting for the position of the cart along the track as point Y; and (x) calculating the distance between point X and point Y, to determine the thickness of the body part in one direction such as the horizontal x-direction. The track can then be rotated 90 degrees (vertical) and the method repeated to determine thickness of the body part in the vertical y-direction, if desired. Finally, the track can be rotated back to its original horizontal position, the body part turned to one side, and the process repeated to determine thickness of the body part in question in the z-direction if desired.

In the event that the track comprises units of length measurement and the cart comprises a reference point to correspond to the units of length measurement, the step (vi) of accounting for the position of the cart along the track as point X comprises the step noting the unit of length measurement on the track to which the reference point of the cart refers as length X, the step (ix) of accounting for the position of the cart along the track as point Y comprises the step noting the unit of length measurement on the track to which the reference point of the cart refers as length Y, and the step (x) of calculating the distance between point X and point Y comprises the step of calculating the difference between length Y and length X.

BRIEF DESCRIPTION OF THE SEVERAL
VIEWS OF THE DRAWINGS

Figure 2:
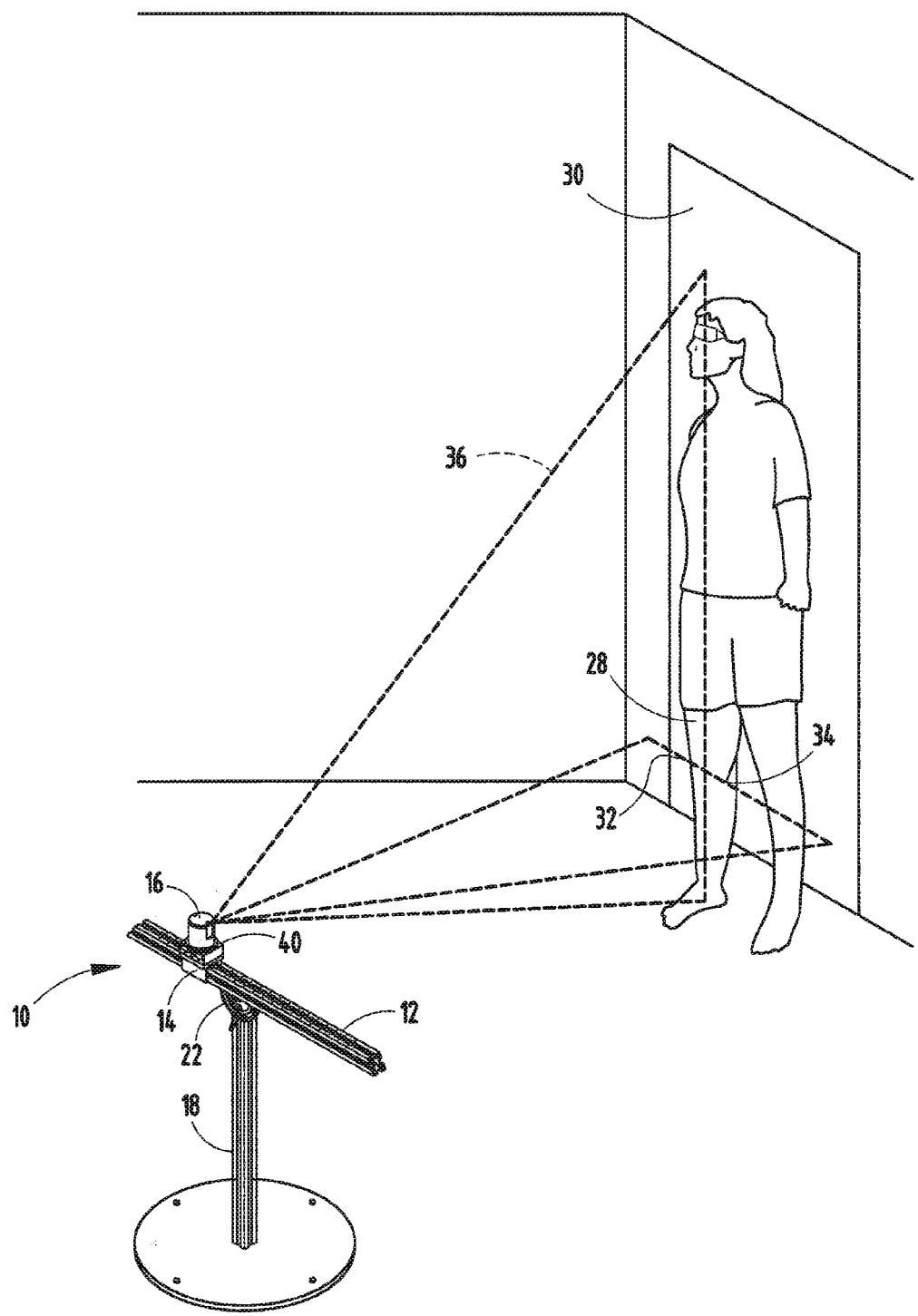
Figure 2A:
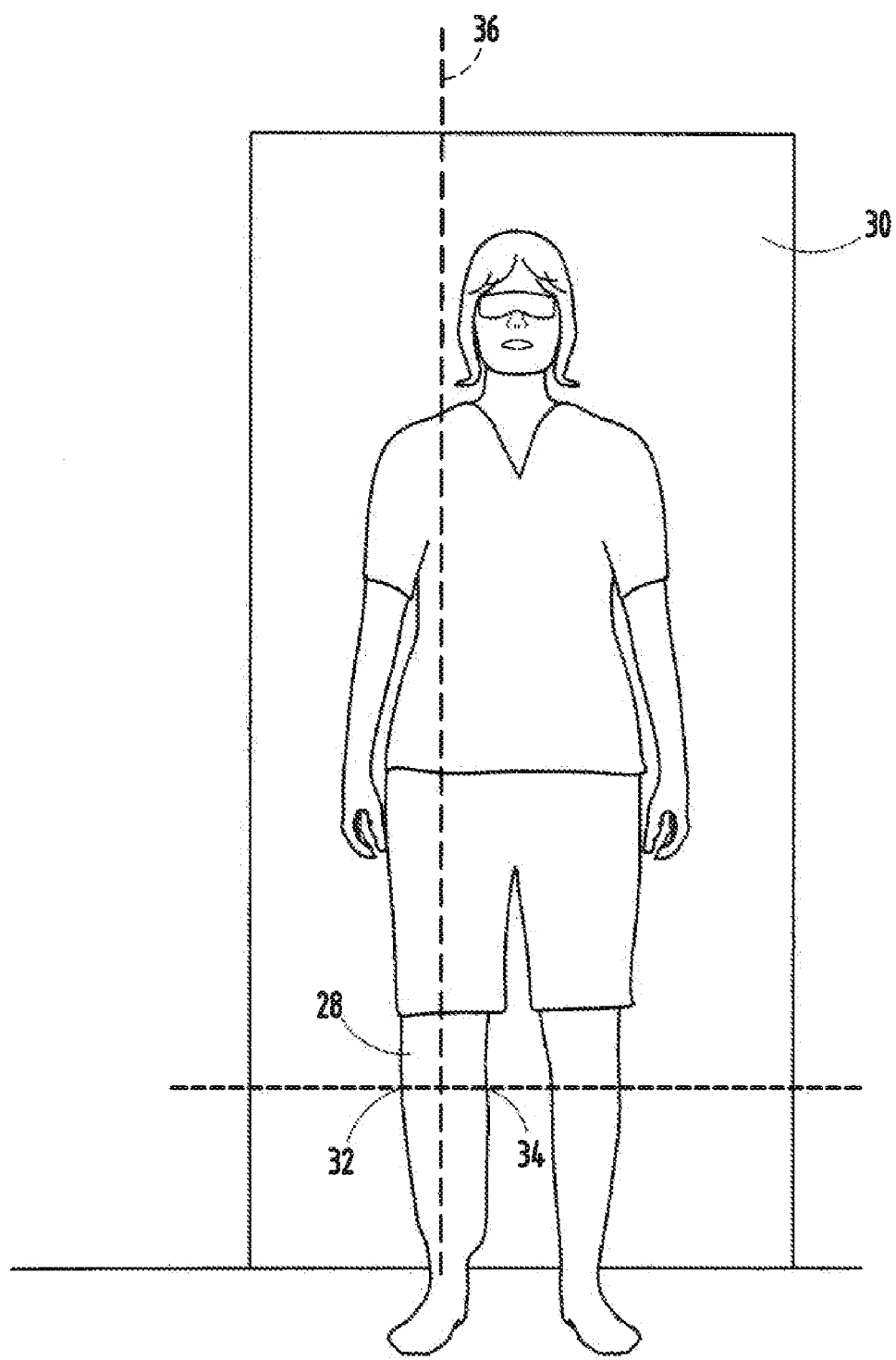

FIG. 2 depicts an embodiment of the body part measurement device 10 emitting laser beam 36 and measuring the body part 28 in front of a screen 30; and FIG. 2A depicts the body part 28 in front of a screen 30.

DETAILED DESCRIPTION OF THE PREFERRED
EMBODIMENTS

Figure 1:
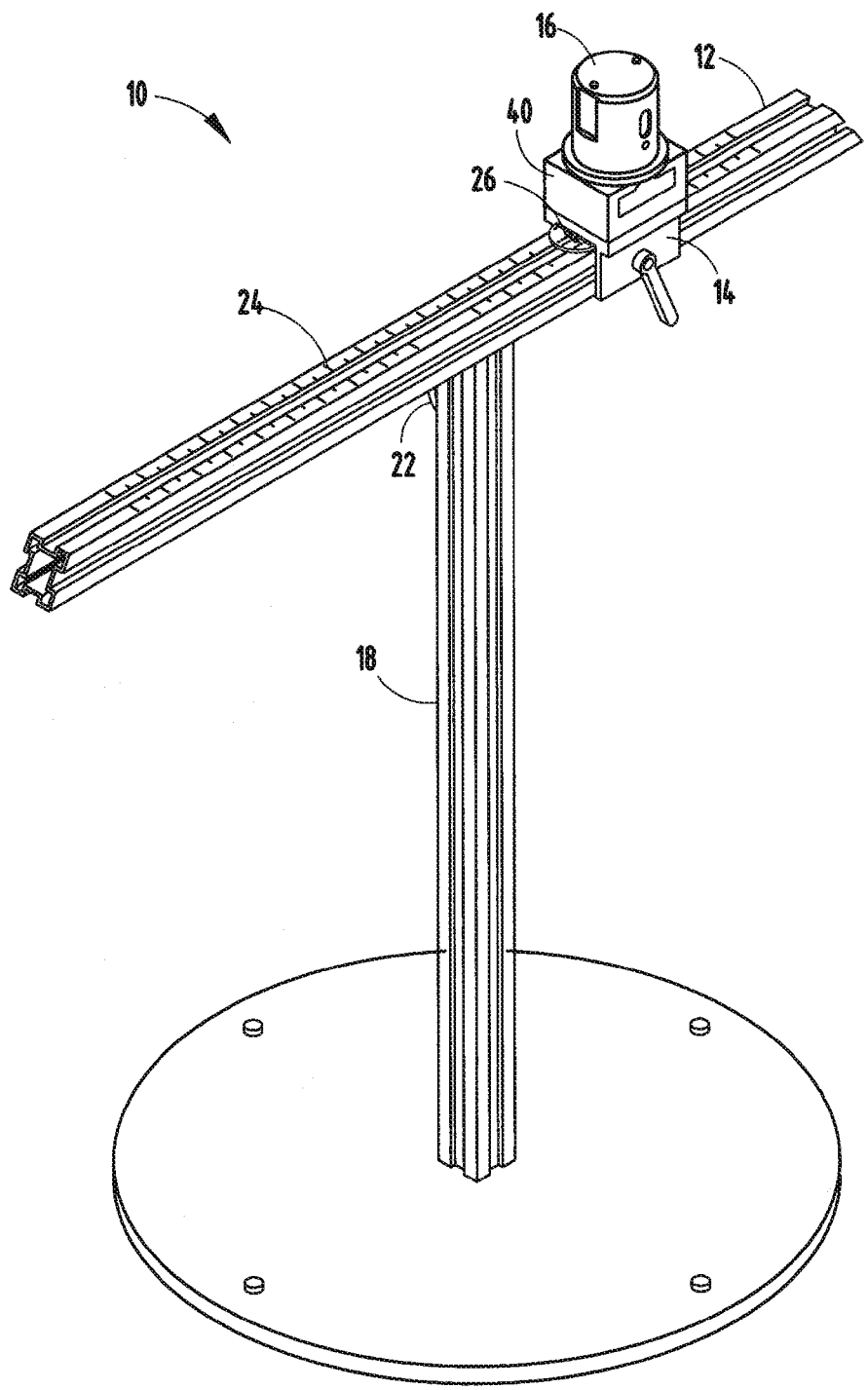
FIG. 1 depicts a perspective view of an embodiment of the body part measurement device 10.

For purposes of description herein, the terms "upper," "lower," "right," "left," "rear," "front," "vertical," "horizontal," and derivatives thereof shall relate to the invention as oriented in FIG. 1. However, it is to be understood that the invention may assume various alternative orientations and step sequences, except where expressly specified to the contrary. It is also to be understood that the specific devices and processes illustrated in the attached drawings, and described in the following specification are exemplary embodiments of the inventive concepts defined in the appended claims. Hence, specific dimensions and other physical characteristics relating to the embodiments disclosed herein are not to be considered as limiting, unless the claims expressly state otherwise.

In an embodiment, body part measurement device 10 (FIG. 1) comprises a track 12 and a cart 14. The cart 14 is capable of linearly moving along the track 12. A laser source 16 is fixedly attached to the cart 14. The laser source 16 can emit a laser beam 36, preferably a cross laser beam (FIG. 2).

Figure 1A:
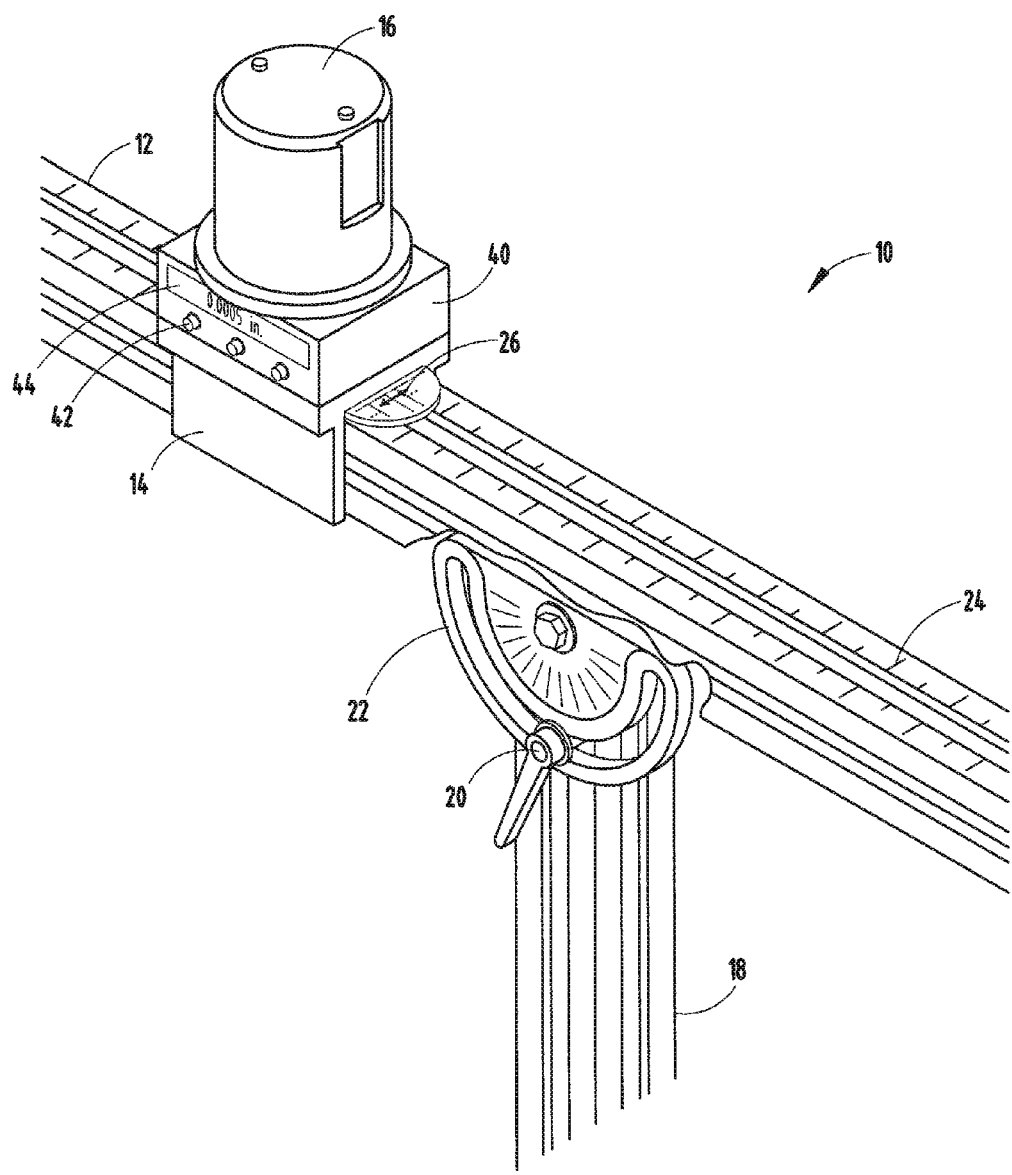
FIG. 1A depicts an enlarged perspective view of an embodiment of the body part measurement device 10.
Figure 1B:
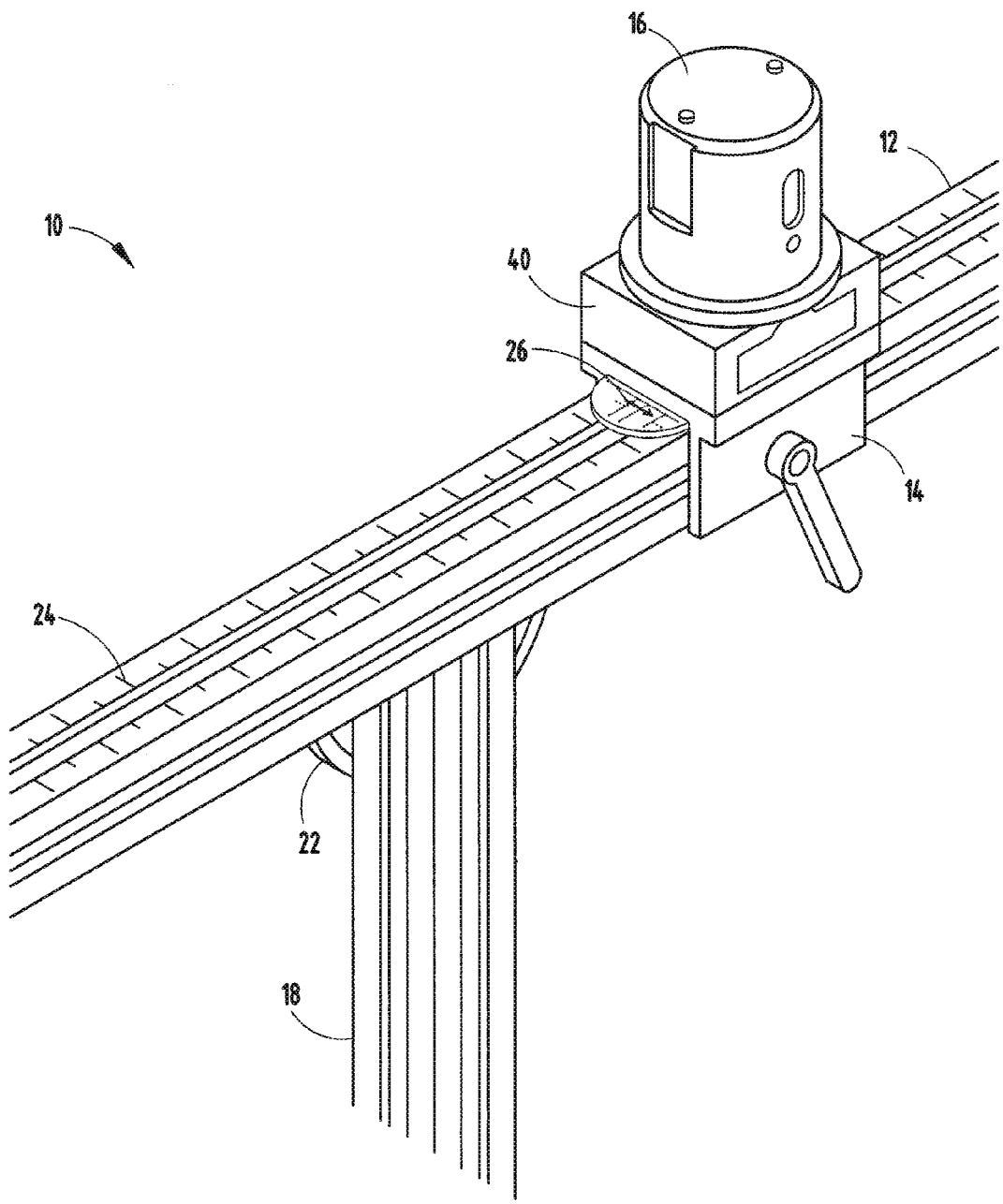
FIG. 1B depicts an enlarged perspective view of an embodiment of the body part measurement device 10.

The body part measurement device 10 can further include a vertical support 18. The vertical support 18 comprises a pivot 20 (FIG. 1A). In such an embodiment, the track 12 then includes a pivot receiver 22, which receives the pivot 20 and allows the track 12 to rotate around the pivot 20. Allowing the track 12 to rotate around the pivot 20 allows measurement of distance at any angle relative to the horizontal.

The track can incorporate units of length measurement 24, such as a ruler that identifies inches units of length measurement. In such an embodiment, the cart can comprise a reference point 26, such as a pointer located above the track 12 to correspond to the units of length measurement 24, to help the user identify one position of the cart 14 relative to a second position of the cart 14. The cart 14 can include an electronic scale 40 (like those found on milling machines or turning centers) that have the ability to zero-out 42 and then measure its own linear travel in small increments (such as increments of 0.0005 inch). In such a case, the cart 14 can have a digital display 44 showing pertinent data (like distance traveled).

A user can use the body part measurement device 10 as part of a method of measuring a body part 28 (FIGS. 2, 2A). In the method, the user presents a body part 28 comprising a thickness defined by a first edge 32 and a second edge 34. The body part 28 is placed between a screen 30 and the body part measurement device 10 which has track 12 oriented parallel to screen 30. The user moves the cart 14 along the track 12 until the laser beam 36 emitted from the laser source 16 appears between the first edge 32 and the second edge 34 of the body part 28. The user then moves the cart 14 along the track 12 so that the laser beam 36 emitted appears to be moving towards the first edge 32 of the body part 28 until the laser beam 36 emitted from the laser source 16 first appears on the screen 30. At this point, the user stops the cart 14 and accounts for the position of the cart 14 along the track 12 as point X. This is a first reference point for determining the thickness of the body part 28. The user then moves the cart 14 along the track 12 towards the second edge 34 of the body part 28 until the laser beam 36 emitted from the laser source 16 first appears on the screen 30. The user then stops the cart 14 and accounts for the position of the cart 14 along the track 12 as point Y. This is a second reference point for determining the thickness of the body part 28. Thus, the user then calculates the distance between point X and point Y and, therefore, has determined the thickness of the body part 28. If the cart 14 has an electronic scale 40 and digital data display 44 showing length, the user can zero-out 42 (FIG. 1A) the scale 40 at point X, move the cart 14 to point Y, and read the data display 44. That would constitute calculation of the distance between point X and point Y.

In the event that the track 12 includes units of length measurement 24 embedded therein, such as a ruler, and the cart comprises a reference point 26 (such as a pointer or edge) to correspond to the units of length measurement 24, the step of accounting for the position of the cart along the track as point X comprises the step noting the unit of length measurement 24 on the track 12 to which the reference point of the cart refers as length X, and the step of accounting for the position of the cart 14 along the track 12 as point Y comprises the step noting the unit of length measurement 24 on the track 12 to which the reference point of the cart 14 refers as length Y. Accordingly, the step of calculating the distance between point X and point Y comprises the step of calculating the difference between length Y and length X.

The track 12 can then be rotated 90 degrees (vertical) and the method repeated to determine thickness of the body part 28 in the vertical y-direction, if desired. Finally, the track 12 can be rotated back to its original horizontal position, the body part 28 turned to one side, and the method repeated to determine thickness of the body part 28 in the z-direction if desired.

The user can record the thickness of the body part 28 in the dimensions measured and the date that the measurement was taken. The user can periodically re-measure the thickness of the body part 28 and compare it to past measurements, to determine whether a particular mode of therapy to decrease the thickness of the body part 28 is working or whether a swelling condition is worsening or developing. The method described herein is beneficial because the user (such as a doctor or nurse) need not actually touch body part 28, which increases safety, privacy, and accuracy of measurement.

In the foregoing description, it will be readily appreciated by those skilled in the art that modifications may be made to the invention without departing from the concepts as disclosed herein. Such modifications are to be considered as included in the following claims, unless those claims by their language expressly state otherwise.

What is claimed is:

1. A body part measurement device comprising:
   a track;
   a cart; and
   a laser source fixedly attached to the cart;
   wherein the cart is supported by the track and is capable of linearly moving along the track in a first direction, and
   wherein the track, cart and laser source are arranged such that the laser source emits a laser beam away from the track and perpendicular to the first direction such that the laser beam moves over the body part to be measured.

2. The body part measurement device of claim 1 further comprising a vertical support for adjustably supporting the track a selected distance above the ground, the vertical support comprising a pivot, the track comprising a pivot receiver, wherein the pivot receiver is rotatably attached to the pivot.

3. The body part measurement device of claim 1, the track comprising units of length measurement.

4. The body part measurement device of claim 3, the cart comprising a reference point to correspond to the units of length measurement.

5. The body part measurement device of claim 1, the cart comprising an internal electronic measurement device that is capable of measuring the distance that the cart has linearly moved along the track, wherein the distance moved along the track corresponds to the body part measurement.

6. The body part measurement device of claim 5, the cart further comprising a digital display capable of showing the distance that the cart has linearly moved along the track.

7. A method of measuring a body part comprising the steps of:
   a. presenting a body part comprising a thickness defined by a first edge and a second edge;
   b. placing the body part between a screen and a body part measurement device comprising:
      a track;
      a cart; and
      a laser source fixedly attached to the cart capable of emitting a laser beam;
      wherein the cart is capable of linearly moving along the track;
   c. moving the cart along the track until the laser beam emitted from the laser source appears between the first edge and the second edge of the body part;
   d. moving the cart along the track so that the laser beam emitted appears to be moving towards the first edge of the body part until the laser beam emitted from the laser source first appears on the screen;
   e. stopping the cart;
   f. accounting for the position of the cart along the track as point X;
   g. moving the cart along the track towards the second edge of the body part until the laser beam emitted from the laser source first appears on the screen;
   h. stopping the cart;
   i. accounting for the position of the cart along the track as point Y;
   j. calculating the distance between point X and point Y to determine the thickness of the body part.

8. The method of claim 7,
   a. the track comprising units of length measurement;
   b. the cart comprising a reference point to correspond to the units of length measurement;
   c. wherein the step of accounting for the position of the cart along the track as point X comprises the step noting the unit of length measurement on the track to which the reference point of the cart refers as length X;
   d. wherein the step of accounting for the position of the cart along the track as point Y comprises the step noting the unit of length measurement on the track to which the reference point of the cart refers as length Y; and
   e. wherein the step of calculating the distance between point X and point Y comprises the step of calculating the difference between length Y and length X.

9. The method of claim 7, the cart comprising an internal electronic measurement device that is capable of measuring the distance that the cart has linearly moved along the track and a digital display capable of showing the distance that the cart has linearly moved along the track,
   a. wherein the step of accounting for the position of the cart along the track as point X comprises the step of zeroing-out the internal electronic measurement device of the cart;
   b. wherein the steps of accounting for the position of the cart along the track as point Y and calculating the distance between point X and point Y to determine the thickness of the body part comprise the step of reading the digital display.

10. The body part measurement device of claim 5, wherein the internal electronic measurement device includes a detector for detecting reflections of the laser beam, wherein such reflections of the laser beam change in a distinguishable manner as the laser beam moves from striking a background to striking the body part to be measured such that the internal electronic measurement device may determine that the distance the cart moved along the track corresponds to the body part measurement.

* * * * *